(12) United States Patent
Lai et al.

(10) Patent No.: US 6,727,362 B1
(45) Date of Patent: Apr. 27, 2004

(54) COUMARIN DERIVATIVES AND AN ELECTROLUMINESCENT (EL) DEVICE USING THE COUMARIN DERIVATIVES

(75) Inventors: Jun-Liang Lai, Taipei (TW); Jih-Sheng Shiu, Taipei (TW); Chih-Wei Kuo, Taipei (TW); Ling Lu, Taipei (TW)

(73) Assignee: Labeltek Inc., Taipei (TW)

( * ) Notice: Subject to any disclaimer, the term of this patent is extended or adjusted under 35 U.S.C. 154(b) by 0 days.

(21) Appl. No.: 10/384,581

(22) Filed: Jun. 19, 2003

(51) Int. Cl.$^7$ .................. C07D 491/12; H05B 33/14
(52) U.S. Cl. .................. 546/66; 428/690; 428/917
(58) Field of Search .............. 546/66; 428/690, 428/917

(56) References Cited

U.S. PATENT DOCUMENTS 6,020,078 A * 2/2000 Chen et al. ............ 428/690

* cited by examiner

*Primary Examiner*—Charanjit S. Aulakh
(74) *Attorney, Agent, or Firm*—Rosenberg, Klein & Lee

(57) ABSTRACT

Coumarin derivatives are used with an electroluminescent (EL) device in accordance with the present invention. The coumarin derivatives have the representative formula (1):

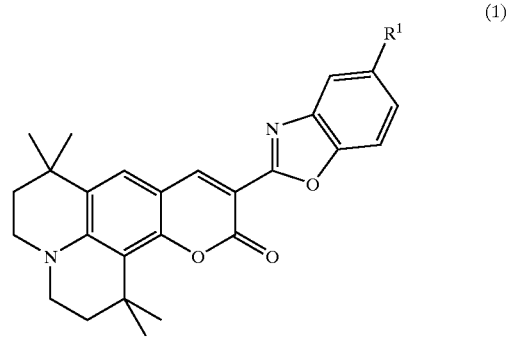

wherein the $R^1$ is a branched alkyl group of 3 to 10 carbon atoms.

4 Claims, 2 Drawing Sheets

COUMARIN DERIVATIVES AND AN ELECTROLUMINESCENT (EL) DEVICE USING THE COUMARIN DERIVATIVES

BACKGROUND OF THE INVENTION

1. Field of the Invention

The present invention relates to coumarin derivatives, and more particularly to coumarin derivatives that, are suitable for use as an organic luminescent material to emit light of a desired color and an electroluminescent device in which the coumarin derivatives are used.

2. Description of Related Art

Organic electroluminescent (EL) material is attracting attention as a substance suitable for flat panel displays because EL material emits light spontaneously, responds at high speeds, and is independent of viewing angles. These features aroused attention about organic electroluminescent materials as a constituent of EL devices. One advantage of organic electroluminescent materials is that they have desired optical properties dependent on their molecular structure. Therefore, producing electoluminescent materials emitting three primary colors (red, green, blue) is possible by changing the molecular structure of the organic electroluminescent materials.

For EL display panels, the organic EL, materials must have the proper chromaticity and sufficient luminance to satisfy basic demands of the EL display panel, and a host-guest doped system offers a ready means of achieving the basic demands. The host-guest doped system is based on the principle of host-guest energy transfer to effect the spectral shift from tris-(8-hydroxyquinolinato)aluminum (Alq) to the dopant molecules of the organic EL materials.

The preferred dopant of the organic EL materials providing green light emissions in the prior art is 3-(2'-benzothiazolyl)-7-diethylaminocoumarin represented by formula coumarin 6 (C-6) and 10-(2-benzothiazolyl)-1,1,7,7-tetrainethyl-2,3,6,7-tetrahydro-1H,5H,11H-[1]benzopyrano[6,7,8-ij]quinolizin-11-one represented by formula coumarin-545T (C-545T). Formula C-6 and C-545T have the following molecular structure:

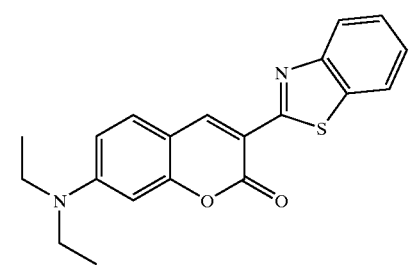

C-6

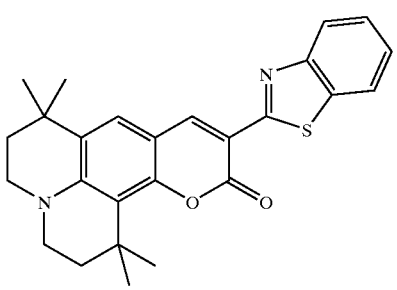

C-545T

These dopants of organic EL materials are fluorescent dyes in an electroluminescent device and have molecules generally with high photoluminescent (PL) quantum yield in dilute solution and high green EL efficiencies when doped at an appropriate concentration level in an EL device using Alq as the host emitter. However, C-6 and C-545T are sensitive to concentration quenching. For example, C-545T drops luminant efficiency when the concentration level is below 1% and is very unstable for passive-matrix display manufacturing.

The present invention has arisen to mitigate or obviate the disadvantages of the conventional organic EL materials.

SUMMARY OF THE INVENTION

A first objective of the present invention is to provide coumarin derivatives that are more resistive to concentration quenching and do not significantly change the chromaticity characteristics.

A second objective of the present invention is to provide an electroluminescent (EL) device comprising at least one organic luminescent layer containing the coumarin derivatives having excellent luminant efficiency.

Further benefits and advantages of the present invention will become apparent after a careful reading of the detailed description with appropriate reference to the accompanying drawings.

BRIEF DESCRIPTION IN THE DRAWINGS

DETAILED DESCRIPTION OF THE PREFERRED EMBODIMENT

Coumarin derivatives in accordance with the present invention are used in emitting layers of electroluminescent (EL) devices and have the following representative formula (1):

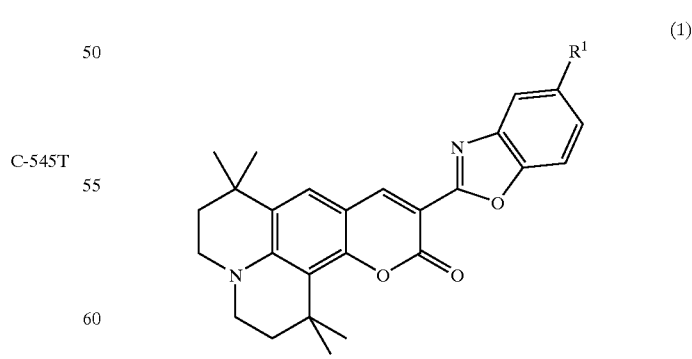

(1)

wherein the $R_1$ is a branched alkyl group of 3–10 carbon atoms where the branched alkyl group is selected from a group of branched groups comprising the following types:

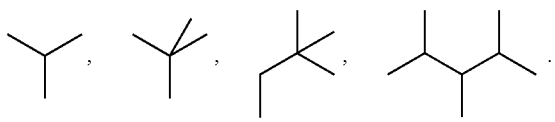

The coumarin derivative in formula (1) is produced by the following equation:

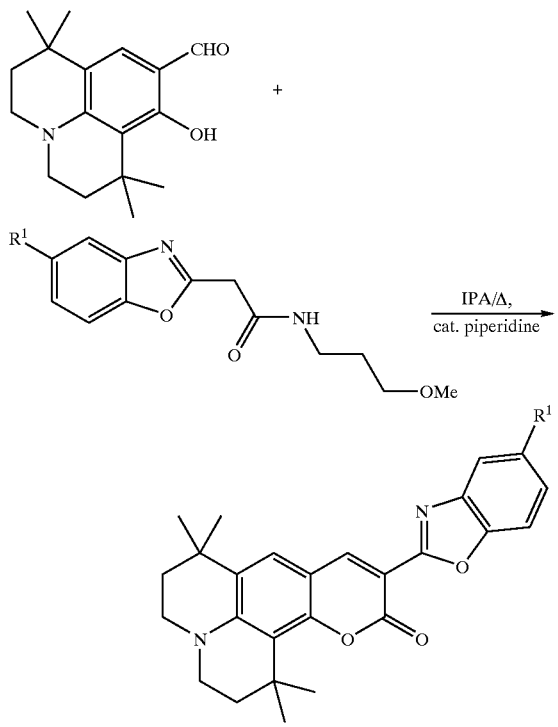

An embodiment of the coumarin derivative, tB-C-525T, is manufactured according to the foregoing chemical equation and has the following formula:

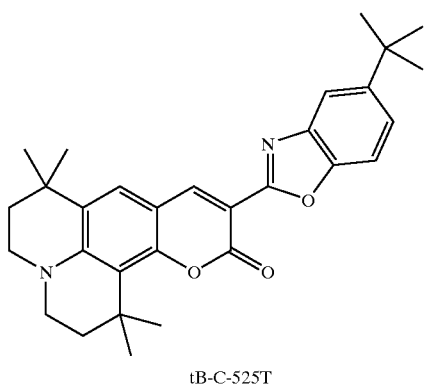

tB-C-525T tB-C-525T has been found to be particularly effective and satisfies the requirements of organic EL material for EL devices.

EXAMPLES

Synthetic Example of tB-C-525T

In a nitrogen atmosphere, 10 g of 1,1,7,7-tetramethyl-8-hydroxy-9-formyljulolidine, 60 ml of iso-propanol, 0.3 g of piperidine and 12.5 g of a composition A were mixed in a reaction container to form a solution. Composition A has the following molecular structure.

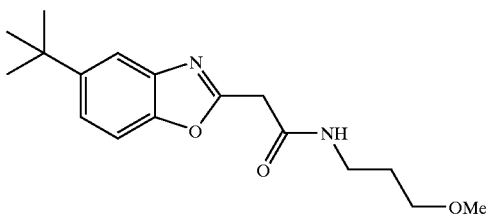

The solution was heated and refluxed for 24 hours and then cooled to crystallize crude tB-C-525T. The crude tB-C-525T was further vaporized and purified to obtain 9.8 g of orange solid tB-C-525T. The physical properties of tB-C-525T follow:

Mass spectrometry: m/e 471(M+)

m.p. (DSC): 200° C.

$T_g$ (DSC): 108° C.

1H-NMR(CDC13) δ 1.28 (6H, s), δ 1.36 (9H, s), δ 1.56 (6H, s), δ 1.73 (2H, m), δ 1.79 (2H, m), δ 3.26 (2H, m), δ 3.35 (2H, m), δ 7.20 (1H, s), δ 7.34 (1H, d), δ 7.46 (1H, d), δ 7.79 (1H, s), δ 8.57 (1H, s).

Figure 1:
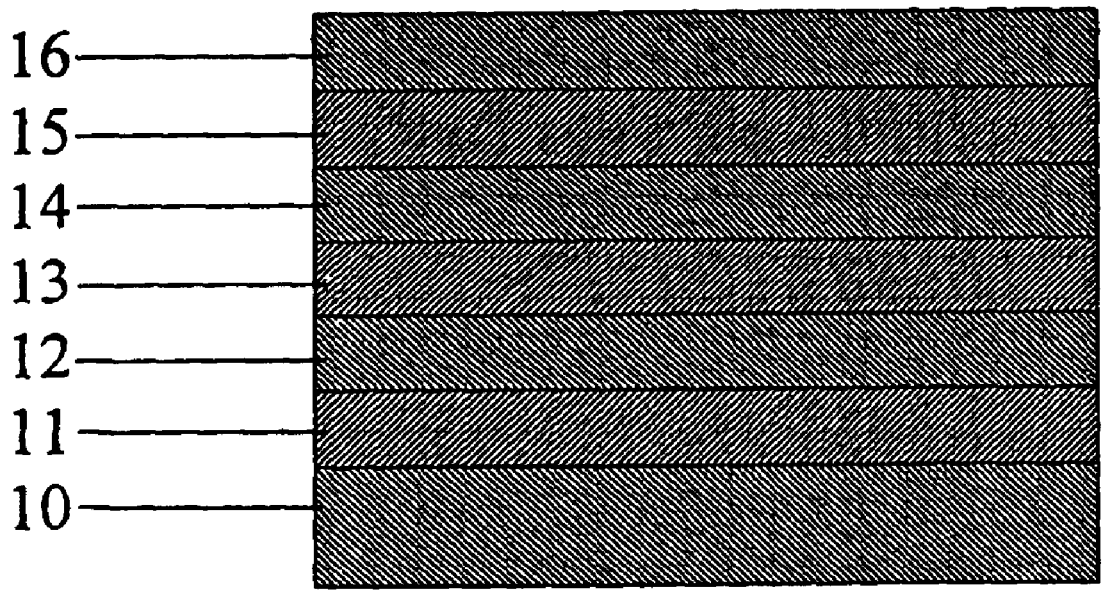
FIG. 1 is a cross sectional side plan view of an electroluminescent (EL) device comprising at least one emitting layer containing organic coumarin derivatives in accordance with the present invention.

An EL device in accordance with the present invention comprises at least one layer containing the coumarin derivative, and the device structure is designed basically to have multiple layers with different functions mounted between a pair of electrodes (anode and cathode) mounted on a transparent substrate. With reference to FIG. 1, a preferred embodiment of the EL device in accordance with the present invention comprises a transparent substrate (10), an anode (11), a cathode (16), a hole transporting layer (12), an emitting layer (13), an electron transporting layer (14) and an electron injection layer (15). The anode (11) is mounted on the transparent substrate (10). The hole transporting layer (12), the emitting layer (13), the electron transporting layer (14) and the electron injection layer (15) are sequentially formed between the anode (11) and the cathode (16).

In the EL device, the hole transporting layer (12), the electron transporting layer (14) and the electron injection layer (15) are not specifically defined to satisfy requirements of their functions so the EL device can be produced in various configurations. In any case, either the anode (11) or the cathode (16) is the first layer formed on the transparent substrate and other layers are formed sequentially on the anode (11) or the cathode (16) in a specific order. Moreover, the anode (11) or the cathode (16) mounted on the transparent substrate (10) are preferred to be made of transparent material so that the light emitted by the EL device can pass through the transparent substrate (10) the side not coated with the multiple layers.

Examples of materials that can be used for each layer of the EL device follow:

The transparent substrate (10) is made of a transparent material such as glass or quartz.

The anode (11) is made of a metal, a metallic alloy or other conductive materials having a work function more than 4eV, such conductive materials are aurum, indium-tin oxide (ITO) and zinc oxide (ZnO).

The cathode (16) is made of a metal, a metallic alloy or other conductive materials having a work function smaller than 4 eV, such materials are lithium, magnesium, calcium, aluminum, aluminum-lithium alloy, and magnesium-silver alloy.

The hole transporting layer (12) is made of an amino-compound composed of nitrogen atoms substituting with three aryl groups. The amino-compound has the following general formula:

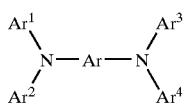

Wherein Ar, $Ar^1$, $Ar^2$, $Ar^3$ and $Ar^4$ are aryl groups.

Two preferred embodiments of the amino-compound of the hole transporting layer (12) follow:

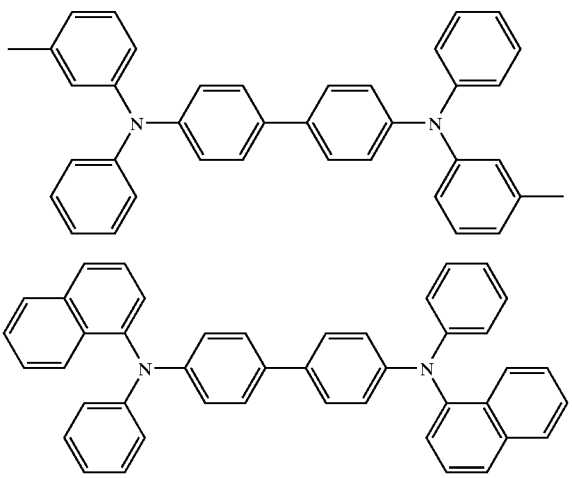

The emitting, layer (13) is made of a host molecule mixed with EL materials. When an EL device is activated electrically with a voltage, the anode (11) generates electrical holes and the cathode (16) generates electrons. Potential difference of the voltage drives the electrical holes toward the cathode (16) and the electrons toward the anode (11). When the electrical holes and the electrons meet in the emitting layer (13), an exciton is produced. Then, the exciton shifts from an excited state to a ground state and light is emitted. The host molecule is tris-(8-hydroxyquinolinato)aluminum (Alq) and can create green light by using a single component. However, when the host molecule mixes with at least one organic luminescent material as a guest composition, emitting efficiency of the emitting layer (13) is significantly increased.

As described detail by Tang et al in *J. Appl. Phys.* 65 (1989) 3610 and *Appl. Phys. Lett.* 70 (1997) 1665, Alq is widely used as the host molecule because it has excellent electric transmission and luminescent features. In this host-guest mixed luminescent system, the exciton shifts from an excited state to a ground state to activate the dopant to luminesce efficiently and stably so that the EL device has excellent stability and efficiently avoids decaying of its luminescent power.

The electron transporting layer (14) is made of Alq-type metal chelates, oxadiazole compounds, thiophene compounds or triazole compounds.

The electron injection layer (15) is made of an inorganic salt such as LiF, CsF, etc.

Additionally, each layer is less than 200 nm thick and formed on the transparent substrate (10) or the previous layer as appropriate by vacuum chemical vapor deposition. The entire EL device is less than 500 nm thick.

Figure 2A:
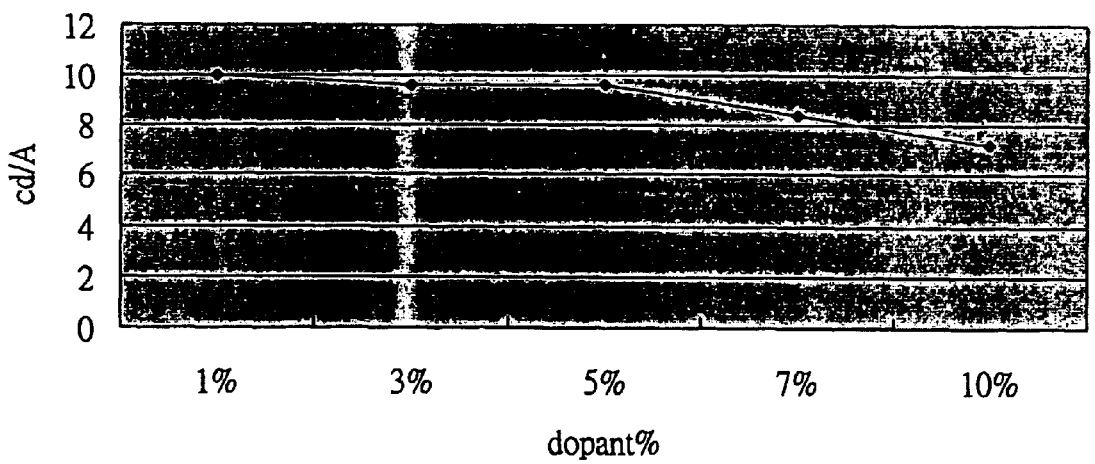
FIG. 2(a) is a chart of luminance efficiency vs. doping concentration of tB-C-525T.
Figure 2B:
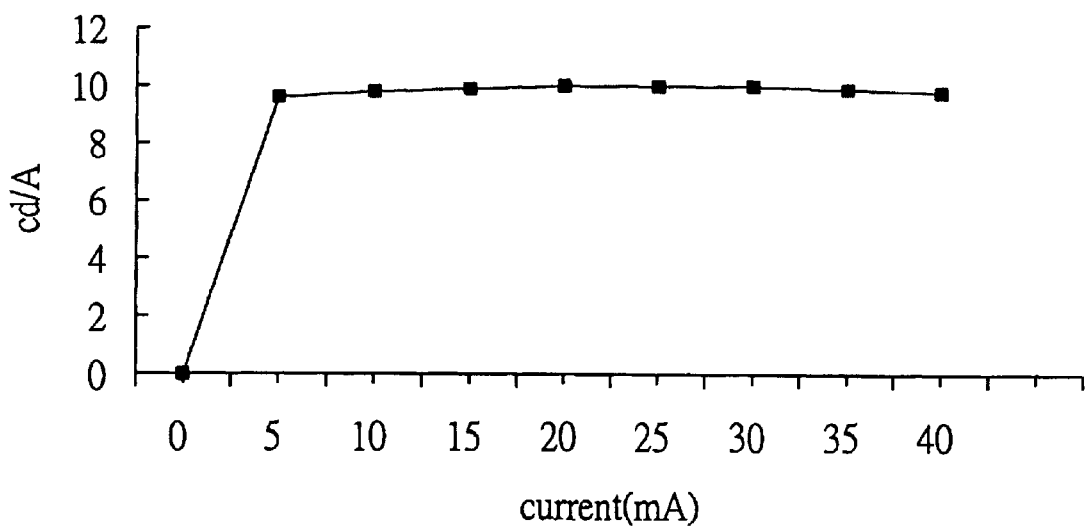
FIG. 2(b) is a chart of luminance efficiency of tB-C-525T vs. current.

Experimental examples of an emitting layer of an EL device:

The coumarin derivative, tB-C-525T, is doped into Alq to form the emitting layer and tested for luminance efficiency. With reference to FIG. 2(a), The luminance efficiency of the emitting layer decreases as the doping concentration of tB-C-525T increases. Dopant tB-C-525T with extra steric spacers keeps the luminance efficiency within 6 to 10 cd/A so the luminance efficiency of tB-C-525T is apparently not sensitive to concentration quenching.

With reference to FIG. (2b), the luminance efficiency (cd/A) of an emitting layer (13) doped with 1% tB-C-525T has a flat response to a wide range of drive current conditions from 5 to 40 mA/cm$^2$. Therefore, the coumarin derivative of tB-C-525T is particularly desirable for the passive-matrix display where the system would need to be capable of high luminance at low voltage and have a flat cd/A responds with respect to drive voltage.

Device Example 1-1

An ITO anode having a surface resistance of 20 ohm per square ($\Omega/\square$) was deposited on a substrate with a commercially available deposition apparatus. A quartz crucible containing N,N'-Di(naphthalen-1-yl)-N,N'diphenyl-benzidine (NPB), a quartz crucible containing Tris-(8-hydroxyquinoline) aluminum (Alq), a quartz crucible containing tB-C-525T synthesized in synthesis example 1, a quartz crucible containing 2,2',2"-(1,3,5-phenylene)tris[1-phenyl-1H-benzimidazole] (TPBI), a graphite crucible containing aluminum and a graphite crucible containing lithium fluoride were placed simultaneously in a vacuum vessel of the deposition apparatus.

The molecular structure of NPB, Alq and TPBI follow:

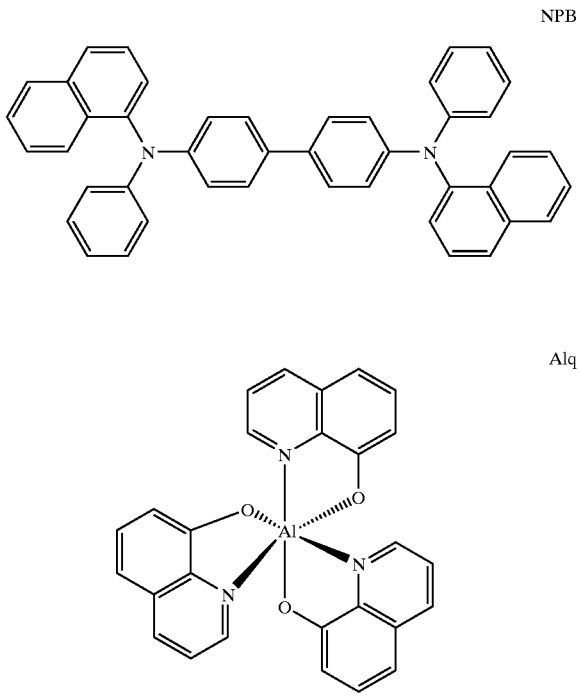

-continued

TPBI

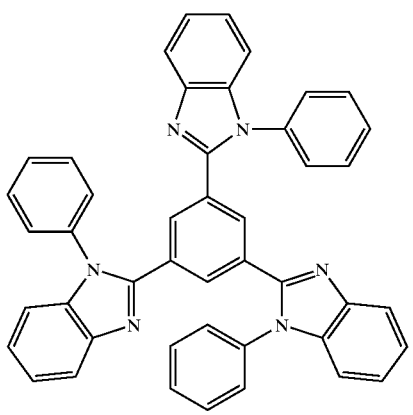

The vacuum vessel was reduced to an internal pressure of $8 \times 10^{-6}$ torr. The crucible containing NPB was heated for vapor deposition to form a hole-transporting layer on the support substrate, wherein the transporting layer of NPB film was 60 nm thick. Then, an emitting layer of doped Alq (30 nm) was deposited onto the hole-transporting layer. The doped layer contained 1% (wt) tB-C-525T that was co-deposited with the Alq to form a uniform doped luminescent emitting layer. An electron-transporting layer of TPBI (20 nm) was then deposited onto the emitting layer.

Subsequently, the graphite crucible containing lithium fluoride was heated for vapor deposition of lithium fluoride to form an electron-injection layer (0.8 nm) on the top of the emitting layer. Finally, an aluminum cathode 150 nm thick was formed on the electron-injection layer.

When a DC voltage of 10 V was applied to the EL device, a light of 26,500 cd/m² was emitted and the EL efficiency was 10 cd/A. The EL color was green with 1931 CIE color coordinates of x=0.28 and y=0.59.

Device Example 1-2

In a manner similar to that used to fabricate the EL device in Example 1-1, an emitting layer was formed by vacuum deposition of Alq doped with 3% (wt) tB-C-525T. When a DC voltage of 10 V was applied to the EL device, a light of 28,000 cd/m² was emitted and the EL efficiency was 9.6 cd/A. The EL color was green with 1931 CIE color coordinates of x=0.28 and y=0.60.

Device Example 1-3

In a manner similar to that used to fabricate the EL device in Example 1-1, an emitting layer was formed by vacuum deposition of Alq doped with 5% (wt) of tB-C-525T. When a DC voltage of 10 V was applied to the EL device, a light of 29,500 cd/m² was emitted and the EL efficiency was 9.6 cd/A. The EL color was green with 1931 CIE color coordinates of x=0.29 and y=0.61.

Device Example 1-4

In a manner similar to that used to fabricate the EL device in Example 1-1, an emitting layer was formed by vacuum deposition of Alq doped with 7% (wt) tB-C-525T. When a DC voltage of 10 V was applied to the EL device, a light of 23,000 cd/m² was emitted and the EL efficiency was 8.4 cd/A. The EL color was green with 1931 CIE color coordinates of x=0.30 and y=0.60.

Device Example 1-5

In a manner similar to that used to fabricate the EL device in Example 1-1, an emitting layer was formed by vacuum deposition of Alq doped with 10% (wt) tB-C-525T. When a DC voltage of 10 V was applied to the EL device, a light of 19,800 cd/m² was emitted and the EL efficiency was 7.2 cd/A. The EL color was green with 1931 CIE color coordinates of x=0.31 and y=0.60.

A review of the foregoing examples of the organic EL device in accordance with the present invention reveals that bright green light organic EL devices were obtained within a large dopant concentration range. Even at a high dopant concentration range of 1% (wt) to 5% (wt), the organic EL devices still have high light emission efficiency without apparent dopant concentration quenching.

The invention has been described in detail with particular reference to certain preferred embodiments. However, it will be understood that variations and modifications can be effected within the spirit and scope of the invention.

Although the invention has been explained in relation to its preferred embodiment, it is to be understood that many other possible modifications and variations can be made without departing from the spirit and scope of the invention as hereinafter claimed.

What is claimed is:

1. Coumarin derivatives having the following representative formula (1):

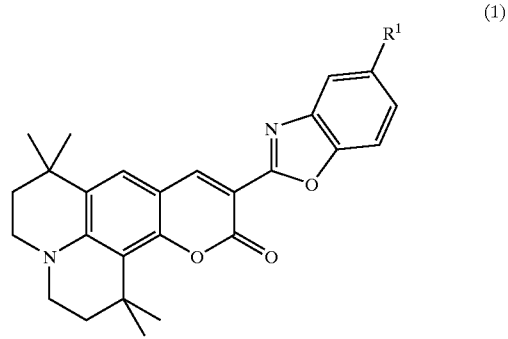

(1)

wherein the R1 is a branched alkyl group of 3 to 10 carbon atoms.

2. The coumarin derivatives as claimed in claim 1, wherein one of the coumarin derivatives is tB-C-525T shown in the following formula:

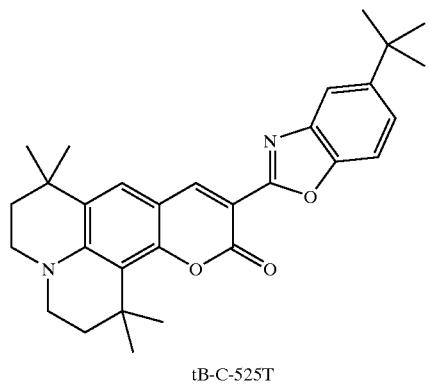

tB-C-525T

3. An electroluminescent (EL) device comprising at least one emitting layer, wherein the at least one emitting layer comprises the coumarin derivative claimed in claim 1.

4. An EL device comprising at least one emitting layer, wherein the coumarin derivative is tB-C-525T claimed in claim 2.

* * * * *